US009526612B2

(12) United States Patent
Board et al.

(10) Patent No.: US 9,526,612 B2
(45) Date of Patent: Dec. 27, 2016

(54) TRANSCATHETER VALVE REPLACEMENT

(71) Applicant: St. Jude Medical, Cardiology Division, Inc., St. Paul, MN (US)

(72) Inventors: Stephanie Marie Board, West St. Paul, MN (US); Aaron J. Chalekian, Savage, MN (US); Patrick P. Russo, Vadnais Heights, MN (US); John Oslund, Blaine, MN (US)

(73) Assignee: St. Jude Medical Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/809,558

(22) Filed: Jul. 27, 2015

(65) Prior Publication Data

US 2015/0327999 A1 Nov. 19, 2015

Related U.S. Application Data

(62) Division of application No. 13/793,818, filed on Mar. 11, 2013, now Pat. No. 9,119,713.

(51) Int. Cl.
*A61F 2/24* (2006.01)
(52) U.S. Cl.
CPC ............ *A61F 2/2427* (2013.01); *A61F 2/2403* (2013.01); *A61F 2/2409* (2013.01); *A61F 2/2418* (2013.01); *A61F 2250/006* (2013.01); *A61F 2250/0069* (2013.01)
(58) Field of Classification Search
CPC ......... A61F 2/2418; A61F 2/2475; A61F 2/24
USPC .................. 623/2.11, 2.15–2.18, 2.38, 2.28, 23.65,623/1.24–1.26
See application file for complete search history.

(56) References Cited

U.S. PATENT DOCUMENTS

| 3,657,744 A | 4/1972 | Ersek |
| 4,423,730 A | 1/1984 | Gabbay |
| 5,843,167 A | 12/1998 | Dwyer et al. |
| 5,924,424 A | 7/1999 | Stevens et al. |
| 5,968,068 A | 10/1999 | Dehdashtian et al. |
| 6,077,297 A | 6/2000 | Robinson et al. |
| 6,306,141 B1 | 10/2001 | Jervis |

(Continued)

FOREIGN PATENT DOCUMENTS

| EP | 1129744 A1 | 9/2001 |
| EP | 1157673 A2 | 11/2001 |

(Continued)

OTHER PUBLICATIONS

International Search Report and Written Opinion for Application No. PCT/US2013/078294 dated Apr. 23, 2014.

(Continued)

*Primary Examiner* — Todd E Manahan
*Assistant Examiner* — Erich Herbermann
(74) *Attorney, Agent, or Firm* — Lerner, David, Littenberg, Krumholz & Mentlik, LLP

(57) ABSTRACT

A prosthetic heart valve having an inflow end and an outflow end includes a collapsible and expandable stent, a collapsible and expandable valve assembly disposed within the stent and having a plurality of leaflets, and a deformable frame having a first end and a second end. The frame includes braided wires forming a body having a lumen extending therethrough for receiving the stent and the valve assembly, the body having a plurality of diameters from the first end to the second end.

18 Claims, 12 Drawing Sheets

(56) References Cited

U.S. PATENT DOCUMENTS

| | | | |
|---|---|---|---|
| 6,425,916 B1 * | 7/2002 | Garrison | A61F 2/2418 623/2.11 |
| 6,623,518 B2 | 9/2003 | Thompson et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 2003/0050694 A1 | 3/2003 | Yang et al. | |
| 2004/0210304 A1 | 10/2004 | Seguin et al. | |
| 2005/0137692 A1 | 6/2005 | Haug et al. | |
| 2005/0137695 A1 | 6/2005 | Salahieh et al. | |
| 2005/0137697 A1 | 6/2005 | Salahieh et al. | |
| 2006/0074484 A1 | 4/2006 | Huber | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2006/0287719 A1 | 12/2006 | Rowe et al. | |
| 2007/0010876 A1 | 1/2007 | Salahieh et al. | |
| 2007/0021826 A1 | 1/2007 | Case et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2008/0051879 A1 | 2/2008 | Case et al. | |
| 2008/0071369 A1 | 3/2008 | Tuval et al. | |
| 2008/0109087 A1 | 5/2008 | Durgin | |
| 2008/0147182 A1 | 6/2008 | Righini et al. | |
| 2008/0177381 A1 * | 7/2008 | Navia | A61F 2/2418 623/2.11 |
| 2009/0054975 A1 | 2/2009 | del Nido et al. | |
| 2009/0248149 A1 | 10/2009 | Gabbay | |
| 2010/0004740 A1 | 1/2010 | Seguin et al. | |
| 2010/0121461 A1 | 5/2010 | Sobrino-Serrano et al. | |
| 2010/0161036 A1 * | 6/2010 | Pintor | A61F 2/2418 623/1.26 |
| 2010/0256751 A1 | 10/2010 | Rowe et al. | |
| 2010/0286768 A1 | 11/2010 | Alkhatib | |
| 2010/0298931 A1 | 11/2010 | Quadri et al. | |
| 2011/0098802 A1 | 4/2011 | Braido et al. | |
| 2011/0137397 A1 | 6/2011 | Chau et al. | |
| 2011/0190905 A1 | 8/2011 | Behan | |
| 2011/0224678 A1 | 9/2011 | Gabbay | |
| 2011/0319991 A1 | 12/2011 | Hariton et al. | |

FOREIGN PATENT DOCUMENTS

| | | |
|---|---|---|
| JP | 2012512718 A | 6/2012 |
| WO | 2007071436 A2 | 6/2007 |
| WO | 2008070797 A2 | 6/2008 |
| WO | 2010051025 A1 | 5/2010 |
| WO | 2010080594 A2 | 7/2010 |
| WO | 2010087975 A1 | 8/2010 |
| WO | 2012127309 A1 | 9/2012 |
| WO | 2012178115 A2 | 12/2012 |
| WO | 2013028387 A2 | 2/2013 |

OTHER PUBLICATIONS

Quaden et al., "Percutaneous aortic valve replacement: resection before implantation", pp. 836-840, European J. of Cardio-thoracic Surgery, 27 (2005).

Ruiz, Carlos, Overview of PRE-CE Mark Transcatheter Aortic Valve Technologies, Euro PCR, dated May 25, 2010.

* cited by examiner

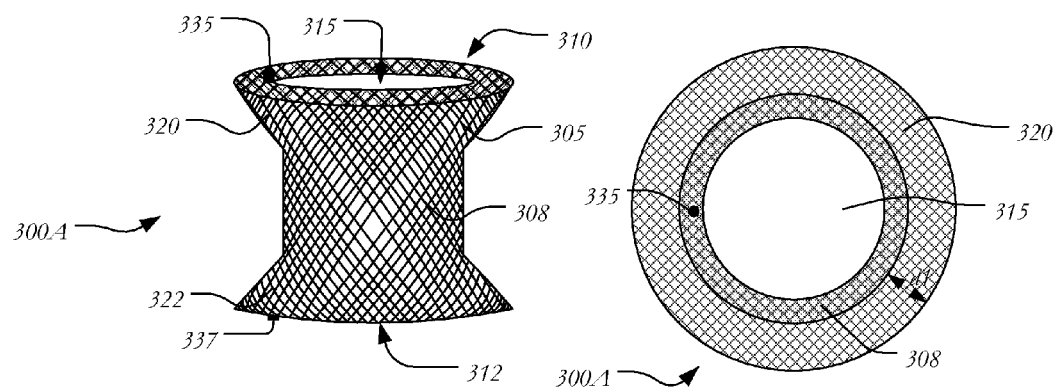
FIG. 5A   FIG. 5B
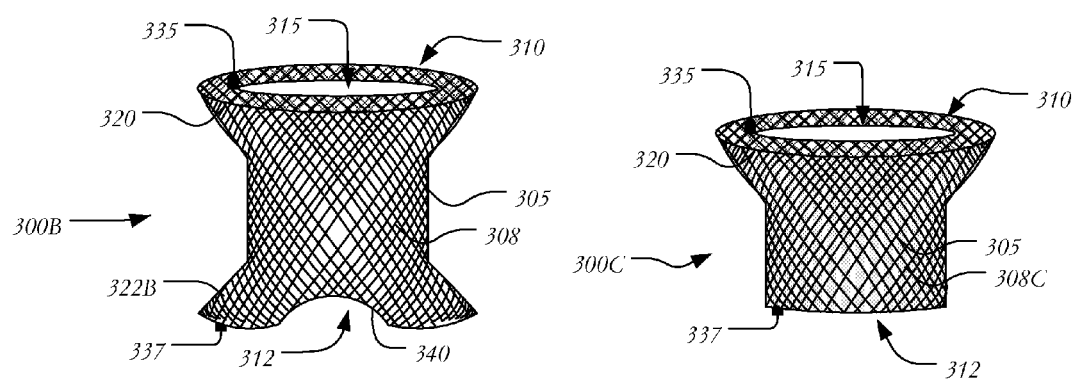
FIG. 5C   FIG. 5D

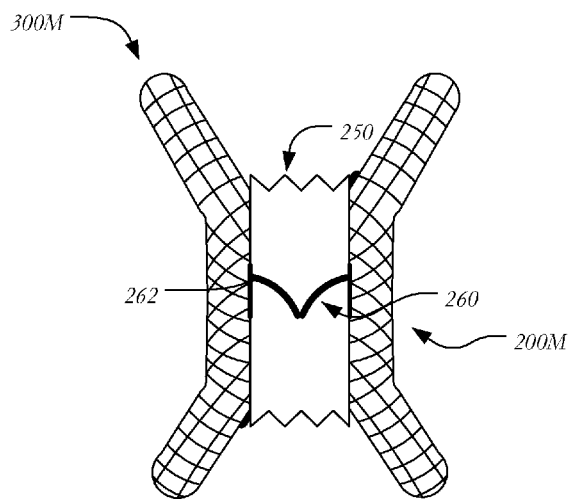
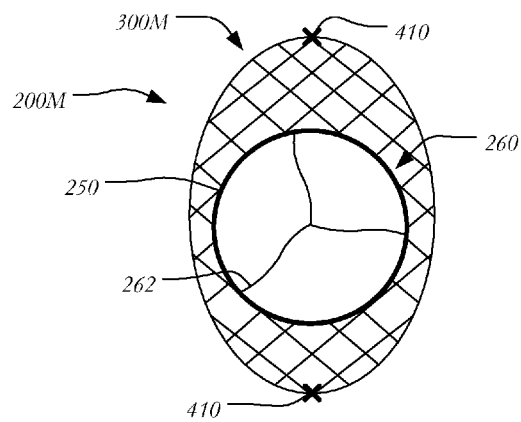
FIG. 7A  FIG. 7B
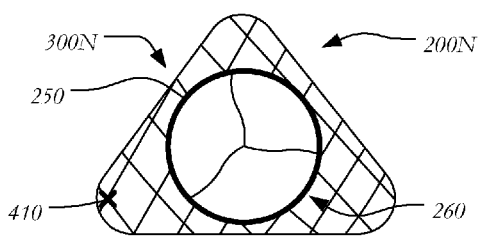
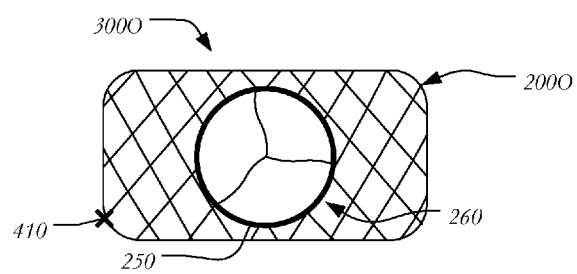
FIG. 7C  FIG. 7D

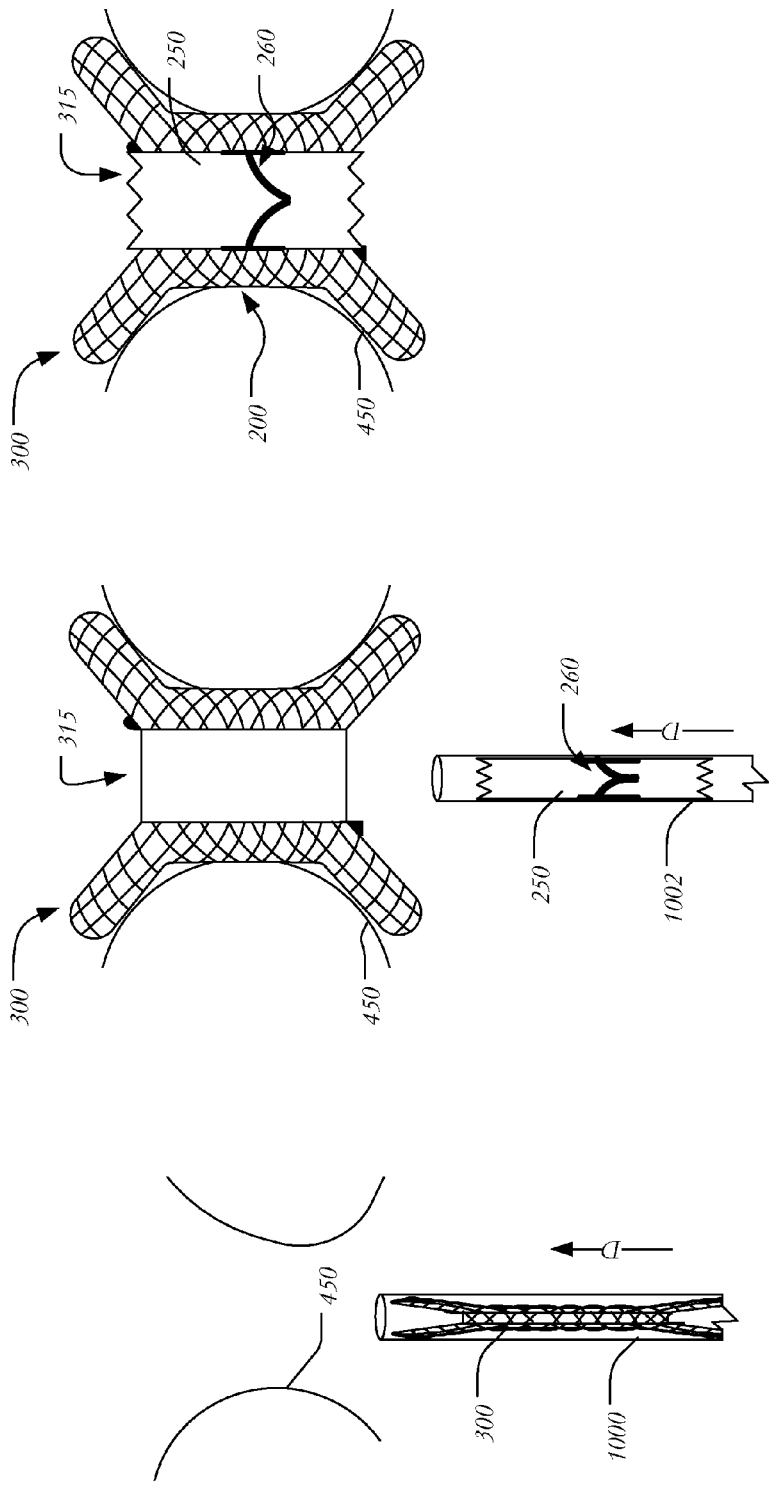

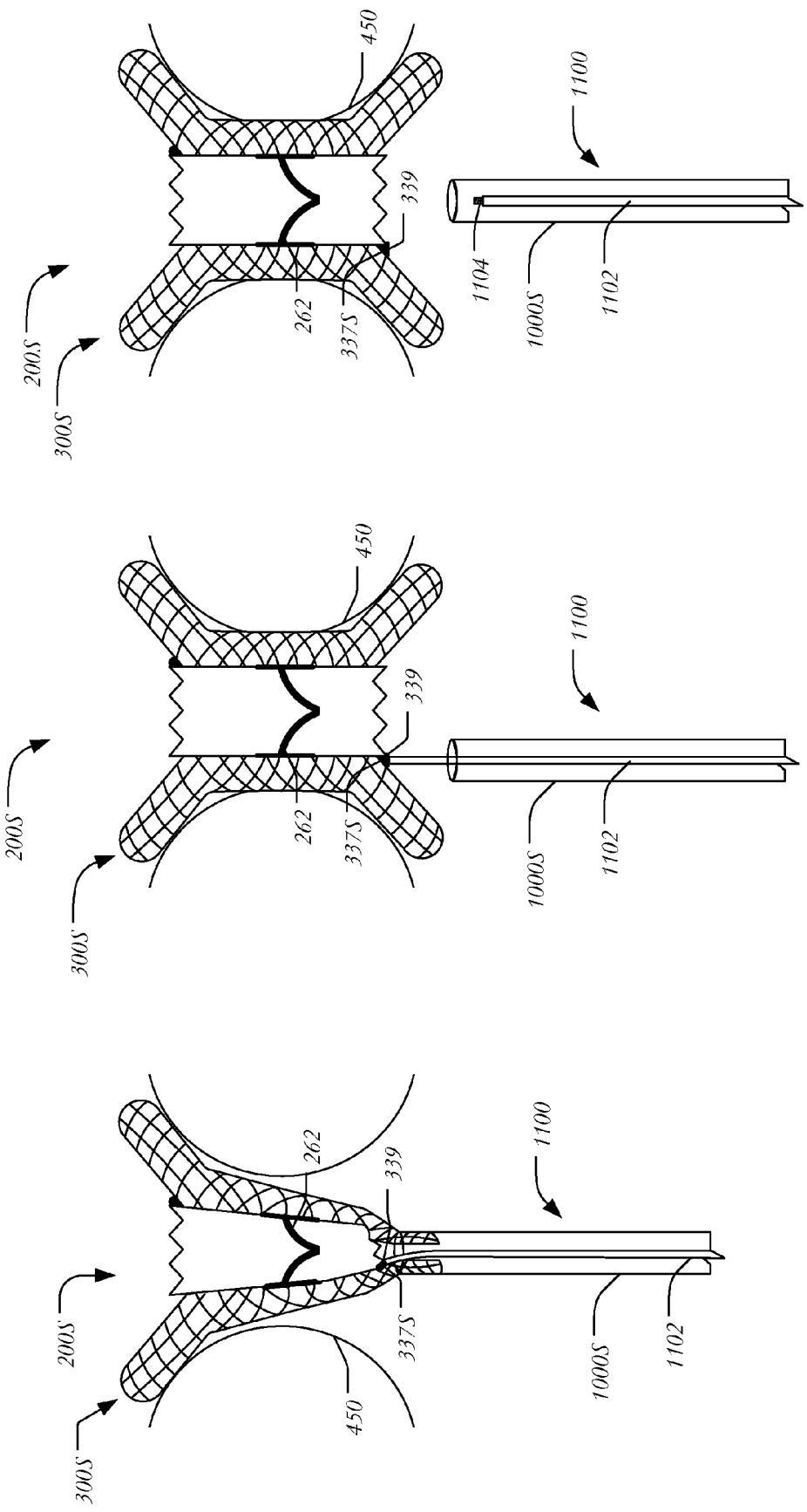

TRANSCATHETER VALVE REPLACEMENT

CROSS-REFERENCE TO RELATED APPLICATIONS

This application is a divisional application of U.S. patent application Ser. No. 13/793,818, filed Mar. 11, 2013.

BACKGROUND OF THE INVENTION

The present disclosure relates to heart valve replacement and, in particular, to collapsible prosthetic heart valves. More particularly, the present disclosure relates to devices and methods for anchoring collapsible prosthetic heart valves within the native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve having an inflow end and an outflow end may include a collapsible and expandable stent and a collapsible and expandable valve assembly disposed within the stent and having a plurality of leaflets. The prosthetic heart valve may further include a collapsible and expandable frame formed of braided wires, the frame having a body portion and a lumen extending through the body portion for receiving the stent and the valve assembly.

In some embodiments, a method of deploying a prosthetic heart valve at a target site is described. The prosthetic heart valve includes a collapsible and expandable stent, a collapsible and expandable valve assembly disposed within the stent, and a collapsible and expandable frame formed of braided wires, the frame having a body portion and a lumen extending through the body portion for receiving the stent and the valve assembly. The method includes deploying the prosthetic heart valve via a delivery device at the target site in a collapsed configuration and allowing the prosthetic heart valve to re-expand at the target site, the prosthetic heart valve being coupled to the delivery device, repositioning the prosthetic heart valve at the target site using the delivery device and decoupling the prosthetic heart valve from the delivery device after evaluating functionality of the prosthetic heart valve.

BRIEF DESCRIPTION OF THE DRAWINGS

Various embodiments of the present disclosure are disclosed herein with reference to the drawings, wherein:

FIG. 5A is a perspective view of another embodiment of a frame having a pair of flanges;

FIG. 5B is a top view of the frame of FIG. 5A;

FIG. 5C is a perspective view of another embodiment of a frame having a pair of flanges and a scalloped lower portion;

FIG. 5D is a perspective view of yet another embodiment of a frame having a shortened length and a single flange;

FIG. 7A is a longitudinal cross-section of a prosthetic heart valve including a frame having a non-circular cross-section;

FIG. 7B is a top view of the prosthetic heart valve of FIG. 7A;

FIG. 7C is a top view of a prosthetic heart valve including a frame having a triangular transverse cross section;

FIG. 7D is a top view of a prosthetic heart valve including a frame having a rectangular transverse cross-section;

FIGS. 10A-C are schematic representations showing the staged-deployment of a prosthetic heart valve; and FIGS. 11A-C are schematic representations showing repositioning and recapture of a prosthetic heart valve using a delivery device.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

Despite the various improvements that have been made to collapsible prosthetic heart valves, conventional devices, systems, and methods suffer from some shortcomings. In conventional collapsible heart valves, the stent is usually anchored within the native valve annulus via the radial force exerted by the expanding stent against the native valve annulus. If the radial force is too high, damage may occur to heart tissue. If, instead, the radial force is too low, the heart valve may move from its implanted position, for example, into the left ventricle, requiring emergency surgery to remove the displaced valve. Because this radial force anchoring partly depends on the presence of calcification or plaque in the native valve annulus, it may be difficult to properly anchor the valve in locations where plaque is lacking (e.g., the mitral valve annulus).

Additionally, in certain situations, as a result of uneven calcification and irregularities in the native valve annulus, blood may leak around the prosthetic heart valve in a condition known as paravalvular leakage. This leakage enables blood to flow from the left ventricle back into the left atrium, reducing cardiac efficiency and putting a greater strain on the heart muscle. Moreover, in certain applications, such as mitral valve replacement, the heart valve may require a lower profile so as not to interfere with surrounding tissue structures. Such a low profile makes it difficult for the valve to remain in place.

In view of the foregoing, there is a need for further improvements to the devices, systems, and methods for prosthetic heart valve implantation and the anchoring of collapsible prosthetic heart valves, and in particular, self expanding prosthetic heart valves. Among other advantages, the present disclosure may address one or more of these needs.

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic heart valve, refers to the end of the heart valve closest to the left ventricle when the heart valve is implanted in a patient.

Figure 1:
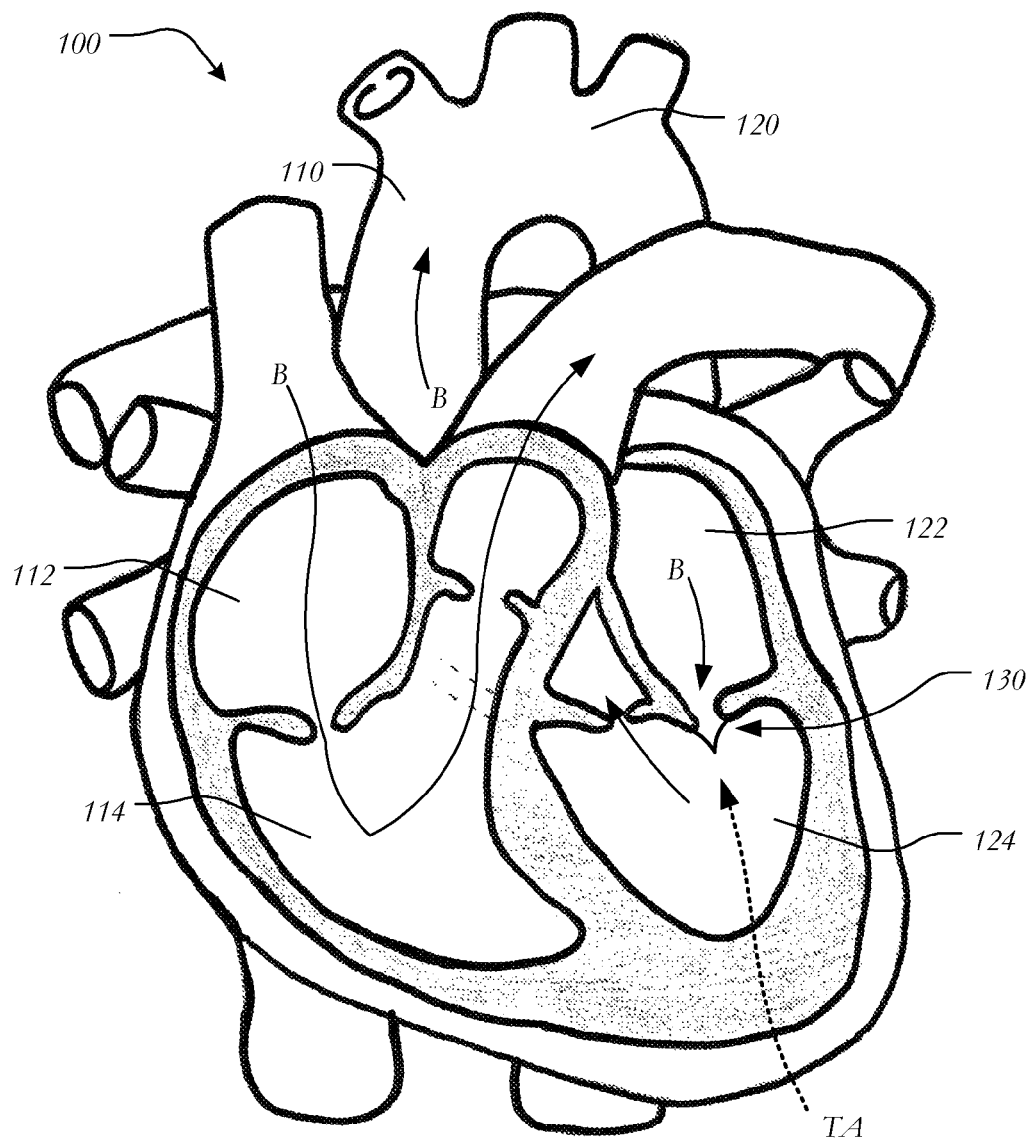
FIG. 1 is a schematic cutaway representation of a human heart showing a transapical delivery approach.

FIG. 1 is a schematic cutaway representation of human heart 100. The human heart includes two atria and two ventricles: right atrium 112 and left atrium 122, and right ventricle 114 and left ventricle 124. As illustrated in FIG. 1, heart 100 further includes aorta 110, and aortic arch 120. Disposed between the left atrium and the left ventricle is mitral valve 130. Mitral valve 130, also known as the bicuspid valve or left atrioventricular valve, is a dual-flap that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled as "TA", indicates a transapical approach of implanting a prosthetic heart valve, in this case to replace the mitral valve. In transapical delivery, a small incision is made between the ribs and into the apex of left ventricle 124 to deliver the prosthetic heart valve to the target site.

Figure 2:
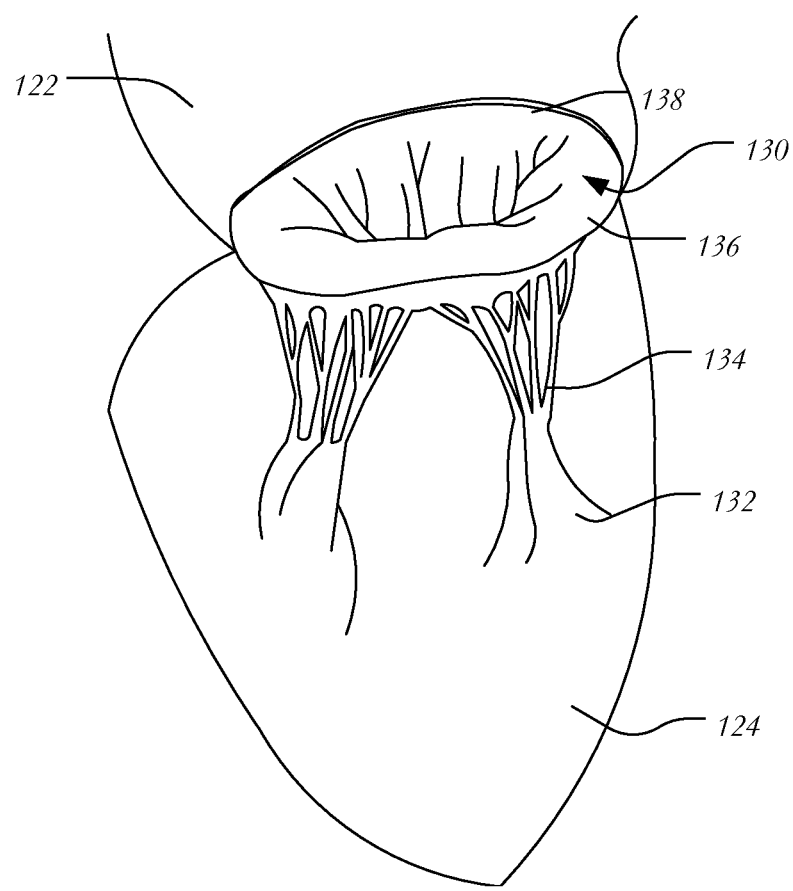
FIG. 2 is a schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cord-like tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower than that in left ventricle 124, leaflets 136, 138 attempt to evert to the low pressure regions. Chordae tendineae 134 prevent the eversion by becoming tense, thus pulling on leaflets 136, 138 and holding them in the closed position.

Figure 3:
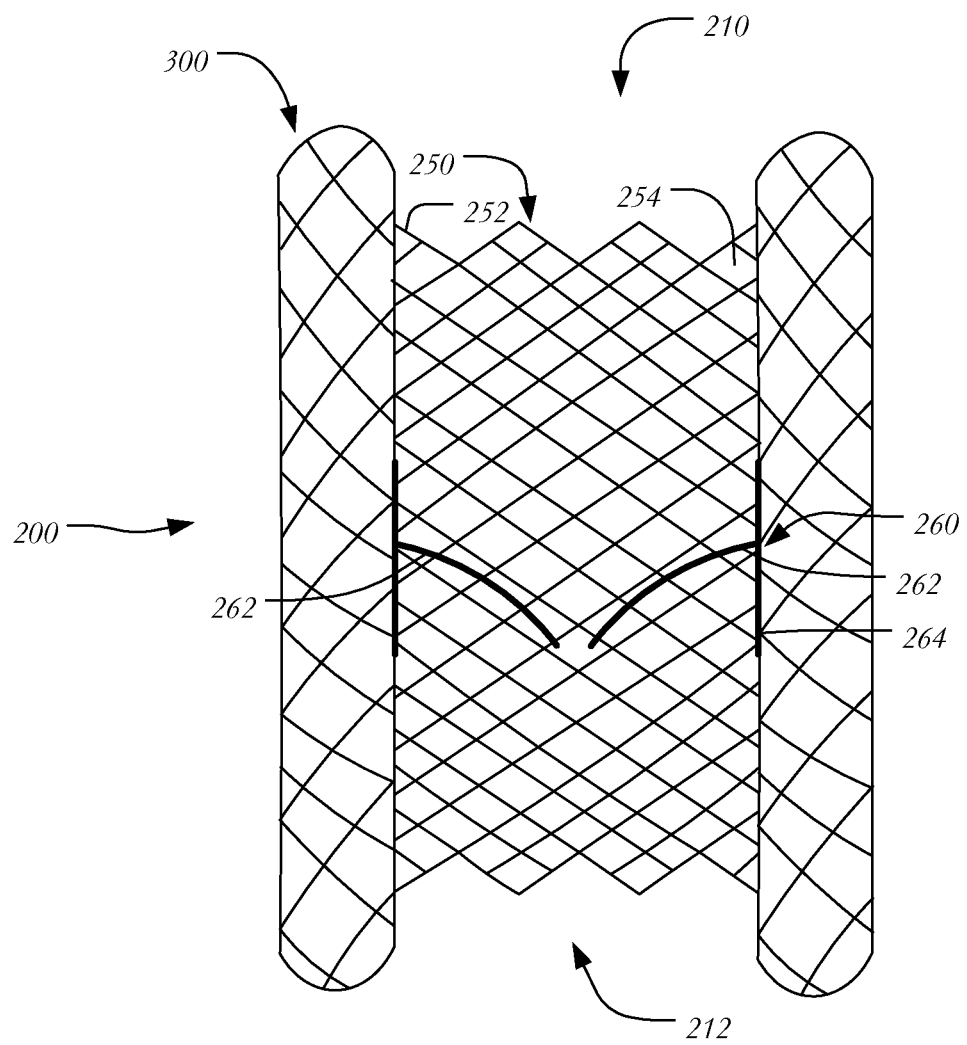
FIG. 3 is a longitudinal cross-section of one embodiment of a prosthetic heart valve having a stent, a valve assembly and a frame.

FIG. 3 is a longitudinal cross-section of prosthetic heart valve 200 in accordance with one embodiment of the present disclosure. Prosthetic heart valve 200 is a collapsible prosthetic heart valve designed to replace the function of the native mitral valve of a patient (see native mitral valve 130 of FIGS. 1-2). Generally, prosthetic valve 200 has inflow end 210 and outflow end 212. Prosthetic valve 200 may be substantially cylindrically shaped and may include features for anchoring, as will be discussed in more detail below. When used to replace native mitral valve 130 (shown in FIGS. 1-2), prosthetic valve 200 may have a low profile so as not to interfere with atrial function.

Prosthetic heart valve 200 may include stent 250, which may be formed from biocompatible materials that are capable of self-expansion, such as, for example, shape memory alloys including nitinol. Stent 250 may include a plurality of struts 252 that form cells 254 connected to one another in one or more annular rows around the stent. Cells 254 may all be of substantially the same size around the perimeter and along the length of stent 250. Alternatively, cells 254 near inflow end 210 may be larger than the cells near outflow end 212. Stent 250 may be expandable to provide a radial force to assist with positioning and stabilizing prosthetic heart valve 200.

Prosthetic heart valve 200 may also include valve assembly 260 including a pair of leaflets 262 attached to a cylindrical cuff 264. Leaflets 262 replace the function of native mitral valve leaflets 136 and 138 described above with reference to FIG. 2. That is, leaflets 262 coapt with one another to function as a one-way valve. It will be appreciated, however, that prosthetic heart valve 200 may have more than two leaflets when used to replace a mitral valve or other cardiac valves within a patient. Valve assembly 260 of prosthetic heart valve 200 may be substantially cylindrical, or may taper outwardly from outflow end 212 to inflow end 210. Both cuff 264 and leaflets 262 may be wholly or partly formed of any suitable biological material, such as bovine or porcine pericardium, or polymers, such as PTFE, urethanes and the like.

When used to replace a native mitral valve, valve assembly 260 may be sized in the range of about 20 mm to about mm in diameter. Valve assembly 260 may be secured to stent 250 by suturing to struts 252 or by using tissue glue, ultrasonic welding or other suitable methods. Alternatively, in embodiments not having a stent, valve assembly 260 may be directly attached to frame 300 using any of the aforementioned methods.

Frame 300 of prosthetic heart valve 200 may surround and house valve assembly 260 and stent 250. Frame 300 may be formed of a braided material, such as nitinol, in various configurations to create varying shapes and/or geometries to engage tissue and fill the spaces between valve assembly 260 and the native valve annulus. Several of these configurations will be described below with reference to FIGS. 4-9.

Figure 4:
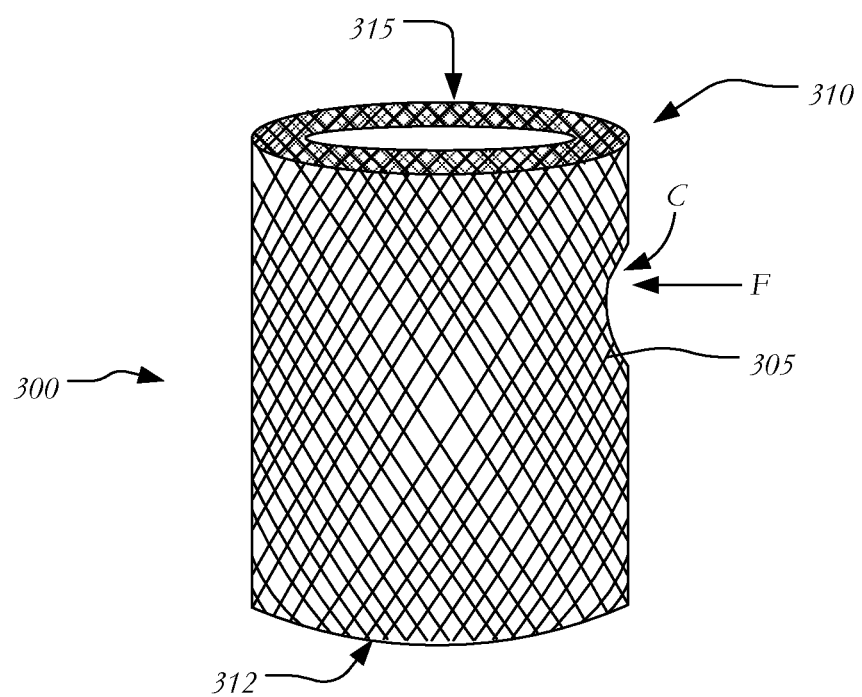
FIG. 4 is a perspective view of the frame of the prosthetic heart valve of FIG. 3.

As shown in FIG. 4, frame 300 includes a plurality of braided strands or wires 305 arranged in three-dimensional shapes. In one example, wires 305 form a braided metal fabric that is both resilient and capable of heat treatment to substantially set a desired preset shape. One class of materials which meets these qualifications is shape memory alloys. One example of a shape memory alloy is Nitinol. It is also understood wires 305 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Depending on the individual material selected, strand diameter, number of strands, and pitch may be altered to achieve the desired properties of frame 300.

In the simplest configuration of frame 300, shown in FIG. 4, frame 300 may be formed in a cylindrical or tubular configuration having inlet end 310, outlet end 312 and lumen 315 extending between inlet end 310 and outlet end 312 for housing stent 250 and valve assembly 260. Frame 300 may be formed of a shape-memory material capable of being radially collapsed from a relaxed or preset configuration to a compressed or reduced configuration for delivery into the patient. Once released after delivery, frame 300 may re-expand to its relaxed or preset configuration. Frame 300 may also be locally compliant in a radial direction such that a force exerted in the direction of arrow F deforms a portion of the frame, as shown by the indented region C. In this manner, irregularities in the native valve annulus may be filled by frame 300, thereby preventing paravalvular leakage. Moreover, portions of frame 300, such as the flanges described below, may endothelialize and in-grow into the heart wall over time, providing permanent stability and a low thrombus surface.

As shown in FIG. 4, frame 300 has been described as having a substantially cylindrical configuration. When prosthetic heart valve 200 utilizes such a frame, radial forces exerted by expanding frame 300, stent 250 and/or valve assembly 260 anchor prosthetic heart valve 200 within the native annulus. In some examples, valve assembly 260 may exert a radial force either in conjunction with or independently of frame 300. It may be possible for frame 300 to include additional features capable of anchoring and sealing a prosthetic heart valve within the native valve annulus, which are discussed below with reference to FIGS. 5A-5D.

FIGS. 5A-D illustrate embodiments of frame 300 having anchoring features. Frame 300 may be formed of a braided wires 305 shaped in a cylindrical or tubular body 308 having inlet end 310, outlet end 312 and lumen 315 extending between inlet and outlet ends 310, 312 for housing stent 250 and valve assembly 260. Frame 300 may further include an upper flange 320 and a lower flange 322 as will be described in greater detail below. As shown throughout FIGS. 5A-5D, free ends of braided wires 305 may be held together at inlet end 310 via first clamp or crimp tube 335 and at outlet end 312 via second clamp or crimp tube 337. In alternative embodiments, free ends are located at only one end of frame 300 and/or secured to prevent unraveling by other means (e.g. solder, braze, weld, or heat set). Crimp tube 337 may be internally or externally threaded or may include other suitable means as recognized by people skilled in the art for releasable connection to a device for delivery and recapture of the prosthetic heart valve. Other means of attachment for frame 300 and a delivery device include press fit, snap fit, compression fit, tethers, hook and clasps or other mechanical mating arrangements. In some examples, crimp tube 337 may be a section of tubing configured such that when a braid or portion of braid or any portion of a device is inserted in the tube, it may be crimped down on the outside by mechanical means thereby securing the two together. The other end of the tube may have a means of attachment such as an internal screw thread to then be able to attach to an externally threaded delivery wire or cable which extends outside the body.

As shown in FIG. 5A, frame 300A may be heat set to form upper flange 320 near inlet end 310 and lower flange 322 near outlet end 312, with a generally cylindrical body portion 308 therebetween. Upper flange 320 may be configured to engage a portion of the left atrium, while lower flange 322 may be configured to engage a portion of the left ventricle and/or papillary muscles (see FIGS. 1-2). Collectively, upper flange 320, lower flange 322 and body portion 308 may form a frame in a spindle or hourglass shape that straddles the mitral valve position, fitting within the native valve annulus to prevent prosthetic heart valve 200 from being dislodged from its intended location. FIG. 5B is a top view of frame 300A from FIG. 5A showing lumen 315 and upper flange 320. It will be understood that the radial distance "$d_1$" by which flanges 320,322 extend from body portion 308 may be varied as desired. Additionally, as seen in FIG. 5A, upper flange 320 may taper outwardly from body portion 308 toward inlet end 310 and lower flange 322 may taper outwardly from body portion 308 to outlet end 312.

FIG. 5C illustrates another embodiment of frame 300B. Frame 300B may be formed of braided wires 305 shaped into body 308 having inlet end 310, outlet end 312 and lumen 315 extending between inlet and outlet ends 310, 312. Frame 300B may further include upper flange 320, lower flange 322B and first and second crimp tubes 335,337. In this variation, lower flange 322B includes scalloped portion 340 in which a portion of braided wires 305 is removed so as to improve the blood flow through outflow end 312 and prevent interference with the left ventricular outflow tract. Scalloped portion 340 may form an inwardly bent outline such that outlet end 312 forms a concave curve as shown in FIG. 5C. Instead of removing material from lower flange 322B to form scalloped portion 340, portions of lower flange 322B may be heat set or otherwise shaped via a mold or other suitable means to form scalloped portion 340 in the configuration shown.

FIG. 5D illustrates frame 300C formed of braided wires 305 shaped into body 308C having inlet end 310, outlet end 312 and lumen 315 extending between inlet and outlet ends 310, 312. Frame 300C may further include upper flange 320 and first and second crimp tubes 335,337. Rather than forming a scalloped portion 340 in flange 322, it will be understood that frame 300C may instead have only an upper flange 320, as shown in FIG. 5D, and a shortened overall length of body 308C to prevent interference with the left ventricular outflow tract.

FIGS. 6A-G illustrate several additional variants of frame 300. In a first variant, shown in FIG. 6A, frame 300D includes upper flange 320D near inlet end 310 and lower flange 322D near outlet end 312, with body portion 308 therebetween. Upper flange 320D and lower flange 322D are both substantially perpendicular to the longitudinal axis L1 of frame 300D, resulting in a spindle-shaped frame. In another variant, shown in FIG. 6B, upper flange 320E and lower flange 322E of frame 300E form about a 45 degree angle with longitudinal axis L1 of frame 300E as indicated by angle r. It will be understood that the angle which upper flange 320 and lower flange 322 form with the axial length of frame 300 may be from greater than 0 degrees to less than 180 degrees. Additionally, it will be understood that upper flange 320 and lower flange 322 need not be symmetric. In other words, the angles that the two flanges form with respect to the longitudinal axis of frame 300 may be different from one another.

Figure 6A:
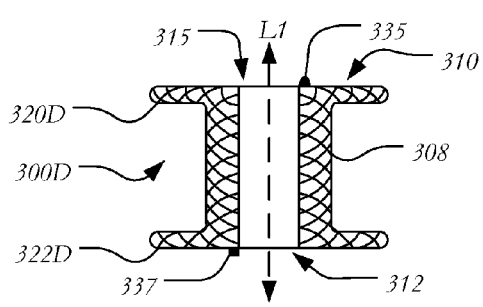
FIGS. 6A-I are longitudinal cross-sections of further variations of the frame of a prosthetic heart valve.
Figure 6B:
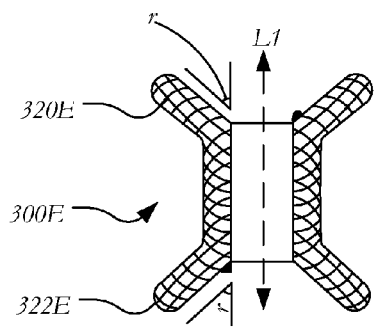
Figure 6C:
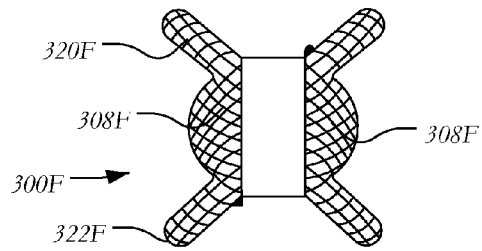
Figure 6D:
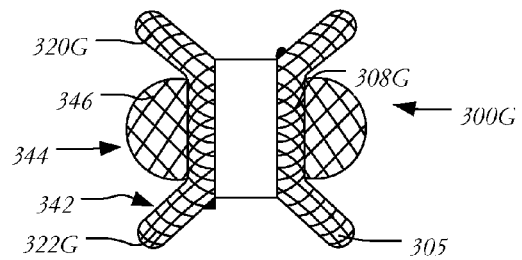

FIG. 6C illustrates frame 300F including upper flange 320F, lower flange 322F and a dilated body portion 308F. Dilated body portion 308F may have a radially expanded shape between upper flange 320F and lower flange 322F that is generally in the form of a sphere, with a longitudinal cross-section that is generally circular. However, it will be understood that other shapes are possible, including those that have longitudinal cross-sections that are triangular, square, rectangular or ovular. Dilated body portion 308F may aid in sealing the prosthetic valve within the native valve annulus and reduce the risk of paravalvular leakage by filling any gaps between the prosthetic valve and the native valve annulus walls with conformable wires 305. In one variation of this construction shown in FIG. 6D, instead of the one-piece frame shown in FIG. 6C, frame 300G may include a first braided portion 342 including upper flange 320G, lower flange 322G and a substantially cylindrical body portion 308G, and a second braided portion 344 disposed about body portion 308G and forming dilated body portion 346.

Figure 6E:
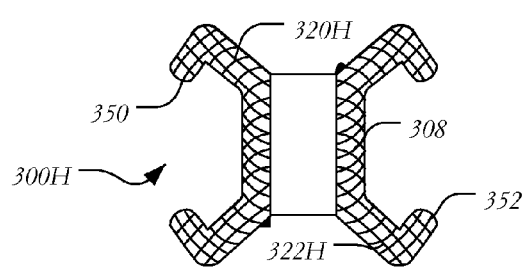
Figure 6F:
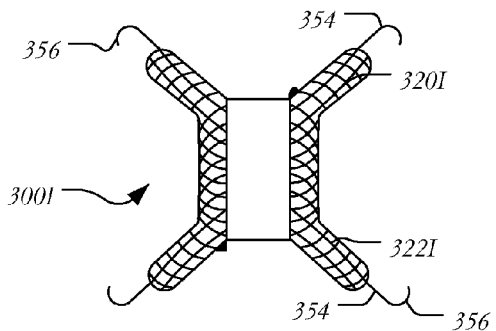
Figure 6G:
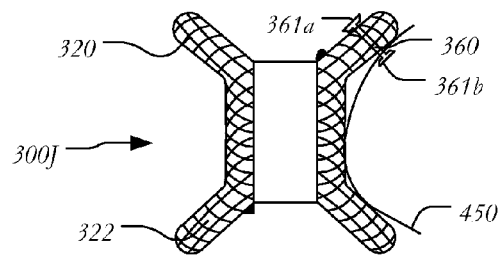
Figure 6H:
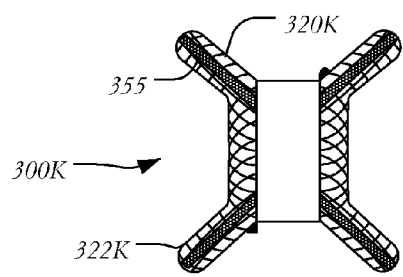
Figure 6I:
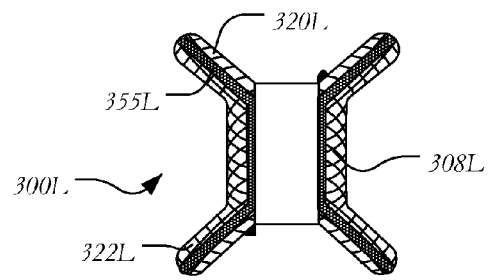

As seen in FIG. 6E-6G, additional features may be added to upper flange 320 and lower flange 322 to improve anchoring. For example, the configurations of upper flange 320 and lower flange 322 may be modified for improved engagement with the native valve annulus. Referring to frame 300H in FIG. 6E, upper flange 320H and lower flange 322H may include secondary bends 350, 352, respectively, for engaging heart tissue. Atrial secondary bend 350 may extend back toward body portion 308 of frame 300H and may be configured to contact a portion of the atrium, while ventricular secondary bend 352 may extend back toward body portion 308 of frame 300H and may be configured to contact a portion of the ventricle. It will be understood that the length and angle of secondary bends 350, 352 may be varied as needed.

Likewise, in order to better anchor frame 300 within the native valve annulus, stabilizing wires 354 may be coupled to upper flange 320I and lower flange 322I as shown on frame 300I in FIG. 6F. Each stabilizing wire 354 may include a barb or hook 356 at its free end. Hook 356 may be manipulated by conventional snares to aid in the delivery of frame 300. Additionally, hooks 356 may be manipulated by one or more snares (not shown) to aid in repositioning frame 300I within the native valve annulus. For example, as will be seen in the following examples, frame 300I may be radially asymmetric and may need to be rotated with the native valve annulus to properly seat the valve assembly. In addition, frame 300I may need to be recaptured and removed for several reasons including improper fitment, inadequate sealing and similar sizing and fitment issues. In such cases, a snare may be used to grasp hooks 356 and pull frame 300 back into a delivery catheter to remove or redeploy the frame.

Moreover, in addition to secondary bends and stabilizing wires, dumbbell-shaped anchors 360 having flared ends 361a, 361b may aid in locking upper flange 320 and/or lower flange 322 to heart tissue 450, as seen in FIG. 6G with respect to frame 300J. Any number of dumbbell-shaped anchors 360 may be used to couple each flange 320, 322 to heart tissue and may be delivered separately to the site of the prosthetic heart valve. Each dumbbell-shaped anchor 360 may pierce through tissue near native valve annulus 450 and through upper flange 320 or lower flange 322, thereby attaching flange 320, 322 to the native tissue. In some examples, anchors 360 may be delivered in the same manner as the heart valve. For example, anchors 360 may be delivered via a catheter and made to pierce upper or lower flange 320, 322, end 361a of anchor 360 may secure one end of the anchor to the flange. Second end 361b of anchor 360 may then be deployed on the tissue side, piercing heart tissue 450 and securing the anchor 360 to the tissue.

To prevent paravalvular leakage, various means could be used to seal flanges 320, 322. In one example, frame 300K shown in FIG. 6H includes reinforcement 355 sewn into the upper and lower flanges 320K, 322K. Reinforcement 335 may comprise polyester strands, braided polystrand, patch materials or a fabric, or any acceptable bio-compatible fabric or other material (including but not limited to: polyester, Polytetrafluoroethylene (PTFE), microporous material formed by stretching PTFE, known as ePTFE). Reinforcement 355 may promote tissue growth, thereby reducing the amount of paravalvular leakage. In another variation, shown as frame 300L in FIG. 6I, reinforcement 355L may be disposed not only in upper flange 320L and lower flange 322L, but also throughout body portion 308L, and may be capable of expanding and collapsing with frame 300L.

Though the previous examples have described frame 300 as having a circular transverse cross-section as shown in FIG. 5B, it will be understood that frame 300 may be modified as desired. For example, FIG. 7A is a longitudinal cross-section of a further embodiment of prosthetic heart valve 200M and FIG. 7B is the corresponding top view thereof. As seen in FIG. 7B, prosthetic heart valve 200M includes frame 300M, with valve assembly 260 having leaflets 262 disposed within frame 300M and supported by stent 250. Valve assembly 260 has a circular transverse cross-section while frame 300M has an oblong transverse cross-section. In many circumstances, the native valve annulus is not circular, but rather is "D-shaped". Due to the non-circular cross-section of frame 300M and the non-circular geometry of the native valve annulus, proper placement of prosthetic heart valve 200M may require a specific orientation. As shown in FIG. 7B, prosthetic heart valve 200M may include one or more markers 410 to aid in such orientation. Markers 410 may include radiopaque structures (e.g., platinum dots or stitches) to allow for visualization of frame 300M within the patient during delivery and/or use. Markers 410 may be disposed on diametrically opposed sides of frame 300M. However, it will be understood that markers 410 may be disposed on any portion of frame 300M, stent 250 and/or valve assembly 260.

FIGS. 7C and 7D illustrate prosthetic heart valves 200 having some other variations of frame 300. In FIG. 7C, prosthetic heart valve 200N includes frame 300N having a triangular transverse cross-section with a circular stent 250 and valve assembly 260 disposed therein. FIG. 7D illustrates prosthetic heart valve 200O having frame 300O with a rectangular transverse cross-section supporting a circular stent 250 and valve assembly 260. One or more markers 410 may be used to determine the orientation of the device as described above.

Figure 8A:
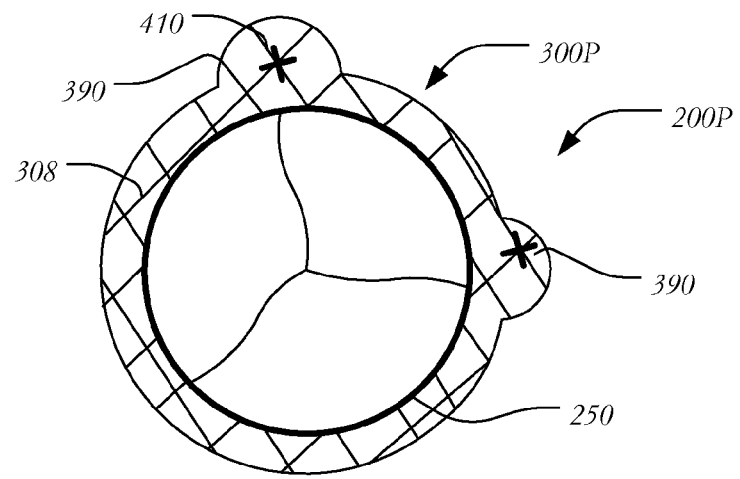
FIGS. 8A and 8B are top views of prosthetic heart valves having frames with irregular cross-sections.
Figure 8B:
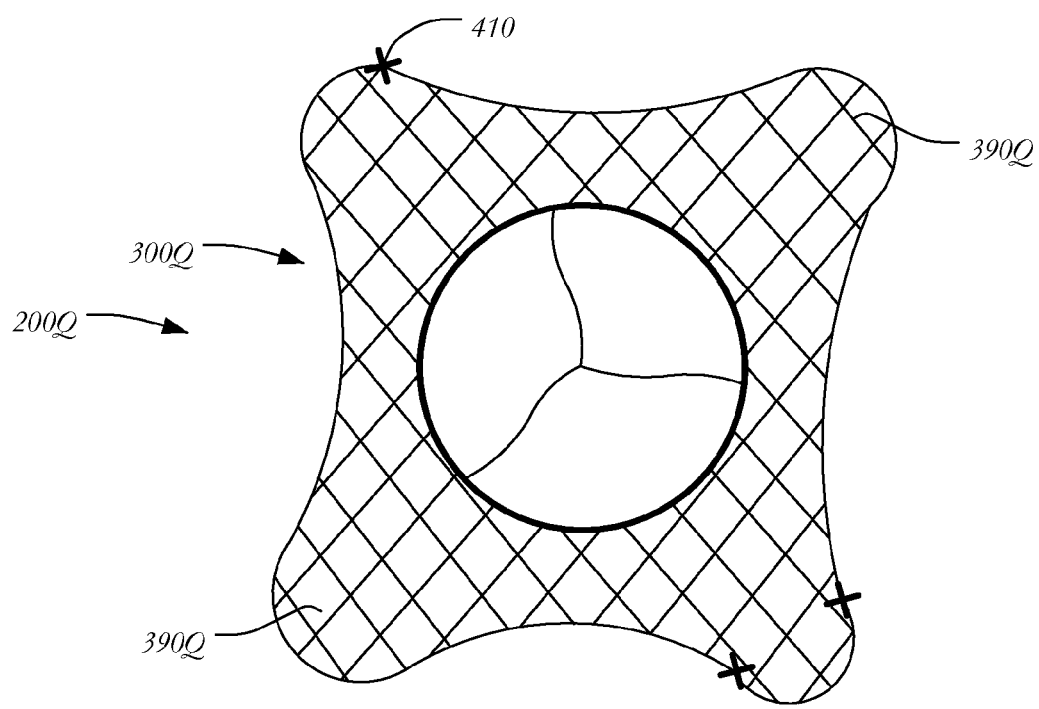

It will be understood that frame 300 need not be limited to basic geometric shapes. For example, FIGS. 8A and 8B are top views of prosthetic heart valves 200 having irregular transverse cross-sections. Frame 300P of FIG. 8A has a substantially circular transverse cross-section and a pair of enlarged regions 390 each having markers 410. Enlarged regions 390 may extend along the length of body 308 and may be continuous therewith. Enlarged regions 390 may aid in providing stability to the anchoring of prosthetic heart valve 200P or in reducing paravalvular leakage. FIG. 8B illustrates another variation in which frame 300Q of prosthetic heart valve 200Q has an irregular cross-section with four enlarged regions 390Q at the corners of the frame. Markers 410 may be disposed on one or more of enlarged regions 390Q to aid in orienting prosthetic heart valve 200Q. Such irregular shapes of frame 390Q may be molded as need and may be useful for preventing paravalvular leakage in an unevenly calcified native valve annulus or in an annulus having an unresected native leaflet.

Figure 9:
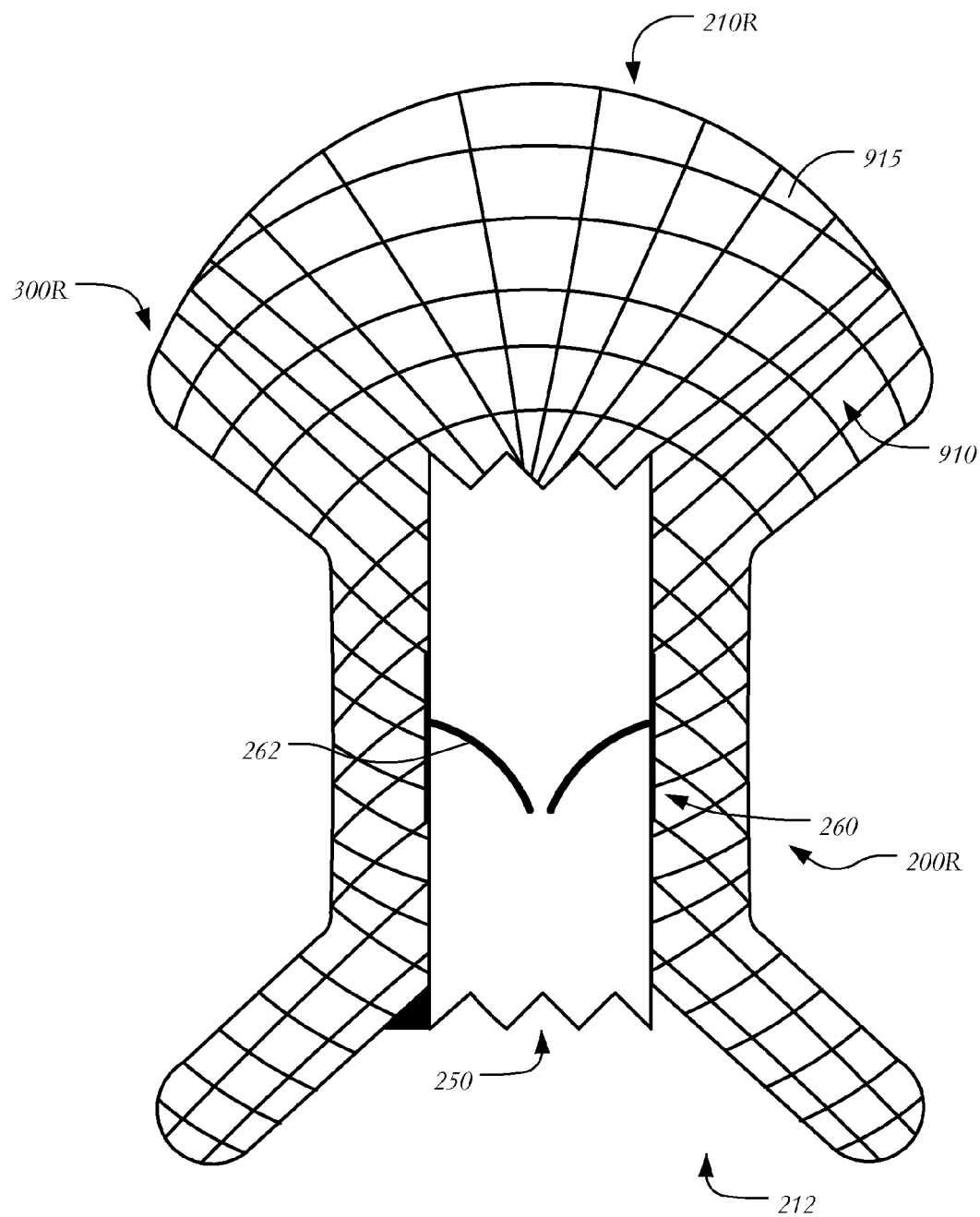
FIG. 9 is a longitudinal cross-section of a prosthetic heart valve including a frame having an inflow crown.

FIG. 9 is a longitudinal cross-section of another variation of prosthetic heart valve 200R. As with the previous embodiments, prosthetic heart valve 200R has an inflow end 210R and an outflow end 212, and includes stent 250, valve assembly 260 having leaflets 262, and braided frame 300R. A portion of frame 300R may be formed into inflow crown 910 instead of upper flanges (compare upper flange 230 of FIG. 5A). Inflow crown 910 may be configured as a generally hemispherical structure made of braided wires 305 shaped to fit within the left atrium when prosthetic heart valve 200R is used to replace a native mitral valve. Inflow crown 910 may be sized to fill a portion of, all of, or substantially all of the left atrium to aid in anchoring prosthetic heart valve 200R within the patient's anatomy. In some variations, the size of inflow crown 910 may be selected based on an analysis of the patient's anatomy. Inflow crown 910 includes a plurality of large pores 915 sized to allow unimpeded blood flow into the left atrium from the pulmonary veins.

The prosthetic heart valves described above may be used to replace a native heart valve, such as the mitral valve, a surgical heart valve or a heart valve that has undergone a surgical procedure. Prosthetic heart valve 200 may be delivered to the desired site (e.g., near a native mitral annulus) using any suitable delivery device. During delivery, the prosthetic heart valve may be disposed inside the delivery device in the compressed configuration. The delivery device may be introduced into the patient using a transapical or other percutaneous approach. For example, prosthetic heart valve 200 may be delivered as an assembled, single unit into the mitral valve annulus to replace the function of a diseased or malfunctioning native mitral valve or previously implanted prosthesis. Specifically, frame 300, stent 250 and valve assembly 260 may be radially collapsed, introduced to the native valve annulus through transcatheter delivery and re-expanded in unison.

Once the delivery device has reached the target site, the user may deploy prosthetic heart valve 200. Upon deployment, prosthetic heart valve 200 expands into secure engagement within the native anatomic structure, such as the mitral valve annulus (shown in FIGS. 1-2), and radial forces keep prosthetic heart valve 200 in place. When prosthetic heart valve 200 is properly positioned inside the patient, it works as a one-way valve, allowing blood to flow in one direction (e.g., from the left atrium to the left ventricle) while preventing blood from flowing in the opposite direction.

Alternatively, prosthetic heart valve 200 may utilize staged-deployment in which the various elements of heart valve 200 are deployed separately and then reassembled within the native valve annulus. Separate delivery of elements, such as illustrated in FIGS. 10A-C, may allow for a reduced delivery profile.

FIG. 10A illustrates a first stage in which a first catheter 1000 is introduced toward the native mitral valve annulus 450. In the depicted embodiment, first catheter 1000 is delivered from the left ventricle in the direction of arrow D through a transapical approach, although other percutaneous approaches are possible. Catheter 1000 houses frame 300, which has been radially collapsed to reduce the delivery profile of the device. Once catheter 1000 has been properly positioned within native valve annulus 450, frame 300 may be pushed out or otherwise released from first catheter 1000 using any suitable method and allowed to radially re-expand into its relaxed configuration, filling native valve annulus 450 and forming lumen 315 (FIG. 10B). At this stage, it may be necessary to adjust frame 300 within native valve annulus 450, for example, to open lumen 315 or to properly orient frame 300 within native valve annulus 450.

Once frame 300 has been properly positioned, a second stage may begin by introducing second catheter 1002 toward native valve annulus 450. Second catheter 1002 may be delivered using the same approach as first catheter 1000, although it will be understood that the two catheters may utilize different approaches. In the illustrated example, second catheter 1002 houses stent 250 and valve assembly 260, both of which have been radially collapsed. Second catheter 1002 may be introduced in the direction of arrow D and the stent and valve assembly combination released inside lumen 315 of frame 300. With stent 250 and valve assembly 260 released from second catheter 1002, the two components may radially self-expand within frame 300, pushing the frame against the walls of native valve annulus 450 while becoming seated and properly secured within the frame via radial forces.

FIG. 10C illustrates prosthetic heart valve 200 after being fully reassembled within native valve annulus 450. When prosthetic heart valve 200 is properly positioned inside the patient, it works as a one-way valve, allowing blood to flow in one direction (e.g., from the left atrium to the left ventricle) and preventing blood from flowing in the opposite direction. Over time, tissue will grow on and into frame 300 and prosthetic heart valve 200 will experience better sealing and anchoring within the native valve annulus.

FIGS. 11A-C illustrate one method of using a delivery device to properly position prosthetic heart valve 200S within native valve annulus 450. Specifically, frame 300S may be configured for partial deployment, resheathing and redeployment from delivery device 1100. Delivery device 1100 may be configured to mate with frame 300S to couple prosthetic heart valve 200S to the delivery device. Delivery device 1100 can take any suitable shape, but desirably comprises a hollow catheter 1000S and an elongate flexible shaft 1102 having an externally threaded distal end 1104 disposed within catheter 1000S. Frame 300S may further include crimp tube 337S having inner thread 339, which is configured to mate with threaded distal end 1104 of shaft 1102. Delivery device 1100 may be used to urge prosthetic heart valve 200S through the lumen of catheter 1000S for deployment in a patient's body. As seen in FIGS. 11A and 11B, when prosthetic heart valve 200S is deployed out the distal end of catheter 1000S, it will still be retained by delivery device 1100 through the coupling of inner thread 339 to threaded distal end 1104. Once prosthetic heart valve 200S is properly positioned within the patient, shaft 1102 can be rotated about its axis to unscrew crimp tube 337S of prosthetic heart valve 200S from threaded distal end 1104 of shaft 1102. Delivery device 1100 including catheter 1000S and shaft 1102 may then be withdrawn (FIG. 11C).

By keeping prosthetic heart valve 200S attached to delivery device 1100, the operator can evaluate the function of leaflets 262 to ensure adequate coaptation and opening. The operator may retract prosthetic heart valve 200S within catheter 1000S for repositioning, even after full deployment from catheter 1000S, if it is determined that prosthetic heart valve 200S is not properly positioned. Thus, if fitment or positioning appears to be incorrect, prosthetic heart valve 200S may be recaptured within catheter 1000S and redeployed, if possible until proper placement is achieved.

It will be appreciated that the various dependent claims and the features set forth therein can be combined in different ways than presented in the initial claims. For example, any combination of flanges, hooks or scalloped portions may be combined in a prosthetic heart valve.

Additionally, a prosthetic heart valve may include any number of markers at any desired location. Additionally, it will be understood that while a transapical delivery approach has been described, the present disclosure contemplates the use of transseptal delivery as well as less conventional approaches, such as direct access to the left atrium or access into the left atrium via the left arterial appendage or the pulmonary veins. It is also conceivable that the device may be delivered by passing through the femoral artery, the aortic valve and the left ventricle. It will be appreciated that any of the features described in connection with individual embodiments may be shared with others of the described embodiments.

For example, the frame may include at least one flange having a transverse cross-section greater than a transverse cross-section of the body portion for anchoring the frame within a native valve annulus. The at least one flange may be adjacent the inflow end of the prosthetic heart valve. The at least one flange may also be adjacent the outflow end of the prosthetic heart valve. The at least one flange may include a secondary bend extending back toward the body portion of the frame.

A stabilizing wire may be disposed on the at least one flange and configured to engage heart tissue. The device may further include a dumbbell-shaped anchor for coupling the at least one flange to heart tissue. The frame may include a scalloped portion adjacent the outflow end of the prosthetic heart valve. The frame may extend in a longitudinal direction between the inflow end and the outflow end of the prosthetic heart valve, the body portion of the frame including a dilated portion having a longitudinal cross-section that is substantially circular. The valve may further include reinforcement coupled to the frame to promote tissue growth. The reinforcement may include polyester strands. The frame may have a non-circular transverse cross-section such as an oblong transverse cross-section.

The heart valve may further include at least one radiopaque marker disposed on at least one of the frame, the stent and the valve assembly. The prosthetic heart valve may be configured to replace a native mitral valve. The valve assembly may include two leaflets. The frame may include a hemispherical inflow crown configured to fit within the left atrium of a patient.

When utilizing the methods described above, the frame, the stent and the valve assembly may be deployed simultaneously. Alternatively, the frame, the stent and the valve assembly may be deployed sequentially. The frame may be deployed using a first catheter and the stent and the valve assembly deployed using a second catheter after the frame is deployed. The target site may be the mitral valve annulus of a patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve having an inflow end and an outflow end, comprising:
   a collapsible and expandable stent having a plurality of struts;
   a collapsible and expandable valve assembly disposed within the stent and having a plurality of leaflets configured to permit a blood flow in a first direction from the inflow end to the outflow end, and to impede the blood flow in a second opposite direction; and
   a deformable frame having a first end and a second end, the frame including a plurality of shape-memory metallic wires that are braided together to form a three-dimensional body defining an inner surface in contact with struts of the stent, an outer surface for contacting native tissue, the body having a thickness between the inner surface and the outer surface, the thickness being variable from a first distance in an uncompressed state, and a second distance when a force is applied to the body, the second distance being less than the first distance, the body having a lumen extending therethrough for receiving the stent and the valve assembly.

2. The prosthetic heart valve of claim 1, wherein the frame further comprises at least one hook configured to engage heart tissue.

3. The prosthetic heart valve of claim 1, wherein the body includes a first diameter and at least one flange having a second diameter that is larger than the first diameter for anchoring the body within a native valve annulus.

4. The prosthetic heart valve of claim 3, wherein the at least one flange is disposed adjacent the outflow end of the prosthetic heart valve.

5. The prosthetic heart valve of claim 3, wherein the at least one flange includes a first section that extends away from the body and a second section that extends back toward the body.

6. The prosthetic heart valve of claim 3, further comprising a stabilizing wire disposed on the at least one flange and configured to engage heart tissue.

7. The prosthetic heart valve of claim 3, further comprising a dumbbell-shaped anchor for coupling the at least one flange to heart tissue.

8. The prosthetic heart valve of claim 1, wherein the frame includes a scalloped portion adjacent the outflow end of the prosthetic heart valve.

9. The prosthetic heart valve of claim 1, wherein the frame extends in a longitudinal direction between the inflow end and the outflow end of the prosthetic heart valve, the body portion of the frame including a dilated portion having a longitudinal cross-section that is substantially circular.

10. The prosthetic heart valve of claim 9, wherein the prosthetic heart valve is configured to replace a native mitral valve.

11. The prosthetic heart valve of claim 9, wherein the valve assembly includes two leaflets.

12. The prosthetic heart valve of claim 1, further comprising a reinforcement coupled to the frame to promote tissue growth.

13. The prosthetic heart valve of claim 12, wherein the reinforcement includes polyester strands.

14. The prosthetic heart valve of claim 12, wherein the frame has a non-circular transverse cross-section.

15. A method of deploying a prosthetic heart valve at a target site, the prosthetic heart valve including a stent having a plurality of struts, a valve assembly disposed within the stent and configured to permit a blood flow in a first direction from the inflow end to the outflow end, and to impede the blood flow in a second opposite direction, and a deformable frame having a first end and a second end, the frame including a plurality of shape-memory metallic wires that are braided together to form a three-dimensional body defining an inner surface in contact with struts of the stent, an outer surface for contacting native tissue, the body having a thickness between the inner surface and the outer surface, the thickness being variable from a first distance in an uncompressed state, and a second distance when a force is applied to the body, the second radial distance being less than the first radial distance, the body having a lumen extending therethrough for receiving the stent and the valve assembly, the method comprising:

deploying the deformable frame at the target site and allowing the frame to expand to fill irregularities in the native valve annulus; and deploying the stent and valve via a delivery device within the expanded frame.

16. The method of claim 15, wherein the target site is the mitral valve annulus of a patient.

17. The method of claim 15, wherein the delivery device comprises a catheter and an inner shaft, the inner shaft being configured to mate with the stent.

18. The method of claim 15, further comprising recapturing the stent within the catheter after expansion at the target site.

* * * * *